United States Patent
Olson et al.

(10) Patent No.: US 6,249,696 B1
(45) Date of Patent: Jun. 19, 2001

(54) METHOD AND APPARATUS FOR INCREASING THE LOW FREQUENCY DYNAMIC RANGE OF A DIGITAL ECG MEASURING SYSTEM

(75) Inventors: Dana J. Olson, Kirkland; David W. Van Ess, Arlington, both of WA (US)

(73) Assignee: Medtronic Physio-Control Manufacturing Corp., Redmond, WA (US)

(*) Notice: Subject to any disclaimer, the term of this patent is extended or adjusted under 35 U.S.C. 154(b) by 0 days.

(21) Appl. No.: 09/232,044

(22) Filed: Jan. 15, 1999

(51) Int. Cl.$^7$ .................................................. A61B 5/0402
(52) U.S. Cl. .......................................... 600/509; 128/901
(58) Field of Search ................................ 607/5; 600/509; 128/901–902

(56) References Cited

U.S. PATENT DOCUMENTS

| | | |
|---|---|---|
| 3,569,852 | 3/1971 | Berkovits . |
| 3,868,567 * | 2/1975 | Ekstrom ............................. 600/509 |
| 4,147,162 | 4/1979 | Gatzke . |
| 4,153,049 | 5/1979 | Gatzke et al. . |
| 4,194,511 | 3/1980 | Feldman . |
| 4,479,922 | 10/1984 | Haynes et al. . |
| 4,494,551 | 1/1985 | Little, III et al. . |
| 4,800,364 | 1/1989 | Mortara . |
| 5,042,026 | 8/1991 | Koike et al. . |
| 5,215,098 * | 6/1993 | Steinhaus et al. .................... 600/509 |
| 5,297,557 | 3/1994 | Reichl . |
| 5,318,036 | 6/1994 | Arand et al. . |
| 5,357,969 | 10/1994 | Herleikson . |
| 5,402,795 | 4/1995 | Reichl . |
| 5,433,208 | 7/1995 | Lundstrom et al. . |
| 5,532,951 | 7/1996 | Ohlsson et al. . |
| 5,601,089 | 2/1997 | Bledsoe et al. . |
| 5,762,068 | 6/1998 | dePinto . |
| 5,772,603 | 6/1998 | Ohlsson et al. . |
| 5,954,660 * | 9/1999 | Legay et al. ......................... 600/509 |

OTHER PUBLICATIONS

Ruha, A., Kostamovaara, J., Saynajakangas, S., "Micropower Analog Structures for CMOS Heart Rate Indicator," Proceedings of the 32$^{nd}$ Midwest Symposium on Circuits and Systems, Aug. 1989, 1990 IEEE, pp. 689–692.

(List continued on next page.)

*Primary Examiner*—Jeffrey R. Jastrzab
(74) *Attorney, Agent, or Firm*—Christensen O'Connor Johnson Kindness PLLC (57) ABSTRACT

An ECG signal measuring system uses low frequency compression/enhancement techniques combined with dither techniques to effectively increase the dynamic range while maintaining resolution. This aspect of the present invention is achieved without increasing the number of bits of the ADC. The system includes a HPF, an ADC, a decimation filter (DF), and a compensation filter (CF). The HPF receives an input signal (i.e., the bias current combined with ECG input signal) and attenuates the low frequency components of the input signal, including a portion of the frequency band within the desired ECG frequency band. The ADC oversamples the output signal of the HPF. The DF receives the output samples of the ADC and generates output samples at rate that is at least twice the maximum frequency of the desired ECG output signal. The CF amplifies the low frequency end of the DF output samples. The gain and cutoff frequency of the CF are set to offset the HPF's attenuation of those low frequency components of the input signal below the minimum frequency of the desired ECG output signal. System noise can be used as the dither. Consequently, the ECG output signal remains within the dynamic range of the system.

25 Claims, 5 Drawing Sheets

OTHER PUBLICATIONS

Leung, S.W., Zhang, Y.T., "Digitization of Electrocardiogram (ECG) Signals Using Delta–Sigma Modulation," Proceedings of the 20th Annual International Conference of the IEEE Engineering in Medicine and Biology Society, vol. 20, No. 4, 1998, pp. 1964–1966.

Vanderkooy, John and Lipshitz, Stanley P., *J. Audio Eng. Soc.*, "Resolution Below the Least Significant Bit in Digital Systems with Dither," vol. 32, No. 3, Mar. 1984.

* cited by examiner

METHOD AND APPARATUS FOR INCREASING THE LOW FREQUENCY DYNAMIC RANGE OF A DIGITAL ECG MEASURING SYSTEM

FIELD OF THE INVENTION

The present invention relates to ECG measuring systems and, more particularly, to ECG measuring systems using analog-to-digital processing.

BACKGROUND INFORMATION

Figures 1, 2:
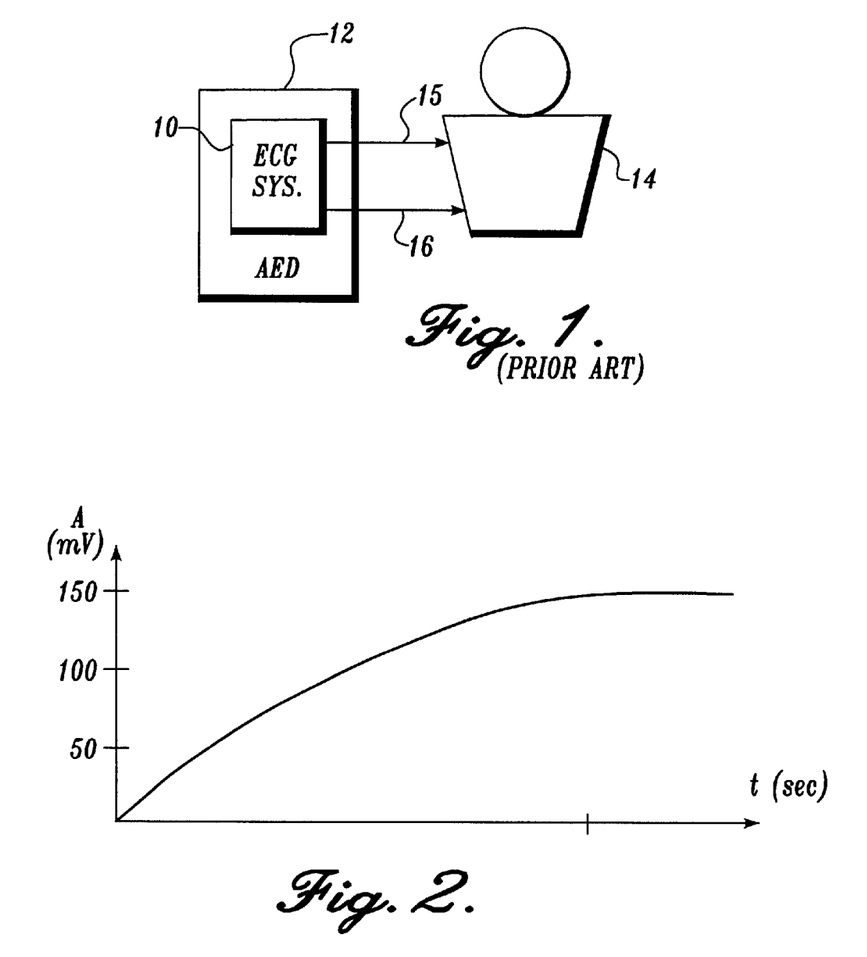
FIG. 1 is a diagram illustrative of a typical ECG signal measuring system.
FIG. 2 is a graph illustrative of an ECG generated by a conventional ECG signal measuring system in applying electrodes to a patient.

When providing emergency cardiac patient care, it is essential to generate the patient's electrocardiograph (ECG) quickly and accurately for proper diagnosis and successful treatment. A typical ECG signal measuring system 10 is shown in FIG. 1. In this example, ECG signal measuring system 10 is part of diagnostic-quality monitor/defibrillator 12. To measure the ECG signal of a patient 14, ECG signal measuring system 10 is coupled to patient 14 through electrodes 15 and 16.

Large amplitude, low-frequency, non-physiological signals, commonly referred to as baseline wander, can saturate an ECG measurement system, resulting in the loss of patient ECG signal information. There are several sources of baseline wander including; DC bias currents, patient movement and changing patient impedance, which are described further below.

ECG signal measuring systems used for emergency medical applications typically use a DC bias current to detect disconnected electrode leads. This current interacts with the patient's impedance to cause a relatively high amplitude but low frequency signal that is superimposed on the relatively low voltage ECG signal when electrodes 15 and 16 are initially applied to patient 14. For convenience, this signal is referred to herein as the bias current signal. This bias current signal is illustrated in FIG. 2 by a curve 20. As can be seen in FIG. 2, an initial portion 21 of curve 20 has a relatively large rate of change. The bias current signal eventually begins to stabilize, as indicated by a portion 23 of curve 20. The bias current signal results in a significant rate of change of the combined input signal (i.e., the baseline wander combined with the patient ECG signal) during the initial period. This rate of change of the combined input signal is referred to herein as the slew rate. When the bias current signal eventually starts to stabilize, the slew rate of the combined input signal is reduced.

A similar problem is caused by movement of patient 14 or electrodes 15 or 16 that disturbs the electrical connection of electrodes 15 and 16 to patient 14. This movement can result in a significant change in the impedance presented to ECG signal measuring system 10. This change in impedance can result in a change in the bias current signal, which results in a slew rate of the combined input signal.

Baseline wander can also be caused by interaction of the bias current with changing patient impedance caused by the electrodes forming a better electrical connection to the patient over time.

Conventional techniques can be used to compensate for the "offset" caused by the baseline wander in order to keep the combined input signal from saturating the system. However, the inventors of the present invention have observed conventional compensation techniques are inadequate for the high slew rate of the combined signal caused during the initial period of the bias current signal.

Figure 3:
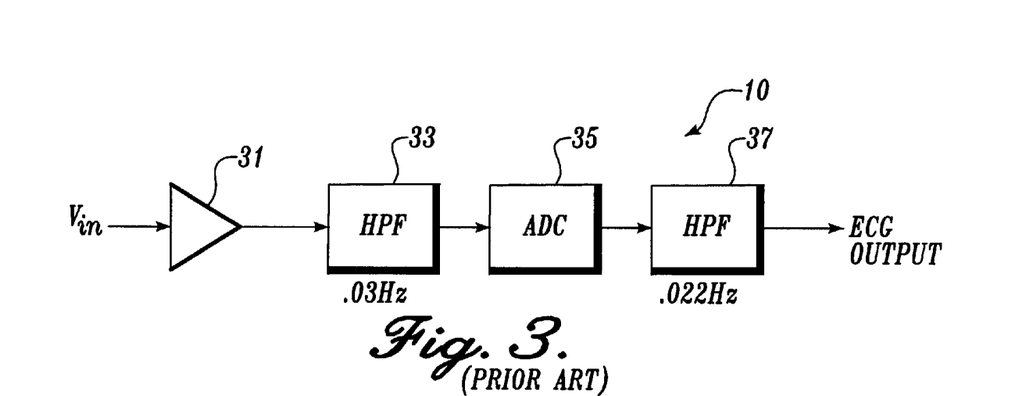
FIG. 3 is a block diagram illustrative of a conventional digital ECG signal measuring system.

FIG. 3 is a block diagram illustrative of conventional digital ECG signal measuring system 10 (FIG. 1). ECG signal measuring system 10 includes a preamplifier 31, a high pass filter (BPF) 33, an analog-to-digital converter (ADC) 35 and a second HPF 37. As will be appreciated by those skilled in the art, ECG signal measuring system 10 includes an anti-aliasing filter (not shown) configured to filter out frequency components of the input ECG signal above one-half of the sample rate of ADC 35.

In this example, the passband of HPF 33 is set at about 0.03 Hz, while the passband of HPF 37 is set at about 0.02 Hz. This gives a passband with a lower edge of 0.05 Hz. This performance is consistent with industry standards for diagnostic quality ECG systems (AAMI EC-11). Unfortunately, the baseline wander signal has frequency components above 0.05 Hz. Thus, in this example, HPF 33 passes the baseline wander signal along with the ECG input signal to cause the saturation problem described above.

One conventional solution to this problem is to increase the dynamic range of the system. Current industry standards require a dynamic range of at least 10 mV (i.e. ranging from ±5 mV). Diagnostic and interpretive algorithms require resolution of 5.0 $\mu$V. This range is adequate for patients ECG signals that do not include baseline wander. Sources of baseline wander discussed above dictate that the dynamic range would have to be increased to greater than 150 mV. However, to increase the dynamic range and maintain a given resolution would require an increase in the number of bits of the analog-to-digital conversion. For example, a twelve-bit ADC can be used for 20 mV dynamic range and 5 $\mu$V resolution. However, a sixteen-bit ADC may be required for 160 mV dynamic range and the same 5 $\mu$V resolution. The cost of a sixteen-bit ADC is significantly higher than a twelve-bit ADC, which undesirably increases the cost of the ECG signal measuring system. Another solution to this problem is disclosed in co-pending and commonly assigned U.S. patent application Ser. No. 09/013, 570, entitled "Digital Sliding Pole Fast Restore For An Electrocardiograph Display," Stice, et al. Although the digital sliding pole invention represents a substantial improvement over the prior art, further improvement is, of course, generally desirable. Thus, there is a need for a low cost ECG measuring system having a relatively large dynamic range and high resolution.

SUMMARY

In accordance with the present invention, an ECG signal measuring system having a relatively large effective dynamic range and high resolution is provided. In one aspect of the present invention, low frequency compression/enhancement techniques are combined with dither techniques to effectively increase the dynamic range while maintaining resolution. This aspect of the present invention is achieved without increasing the number of bits of the ADC.

In one embodiment, the system includes a HPF, an ADC, a decimation filter (DF), and a compensation filter (CF). The HPF receives an input signal (i.e., baseline wander combined with ECG input signal) and attenuates the low frequency components of the input signal. Unlike conventional systems, the HPF serves to attenuate the bias current signal so that the sampled signal remains within the dynamic range of the system. In one embodiment, the HPF attenuates frequency components that are within the frequency bandwidth of the desired ECG output signal. The ADC then oversamples the output signal of the HPF. The DF receives the output samples of the ADC and generates output samples at rate that is at least twice the maximum frequency of the desired ECG output signal. The CF then amplifies the low frequency end of the DF output samples. The gain and cutoff frequency of the CF are, ideally, set to exactly offset the HPF's attenuation of those low frequency components of the input signal below the cutoff frequency of the HPF and above the minimum frequency of the desired ECG output signal. Although it would appear that the resolution of these low frequency components has been degraded, dither techniques are used, in effect, to exchange sample rate for resolution. In one embodiment, system noise (noise inherent in the system due to imperfections in the components, thermal noise, etc.) is used as the dither. As a result of the compression/enhancement and dither techniques, the ECG output signal remains within the dynamic range of the system with the desired resolution, which allows the system to display an accurate ECG significantly faster than conventional systems.

BRIEF DESCRIPTION OF THE DRAWINGS

The foregoing aspects and many of the attendant advantages of this invention will become more readily appreciated by reference to the following detailed description, when taken in conjunction with the accompanying drawings listed below.

DETAILED DESCRIPTION

Figure 4:
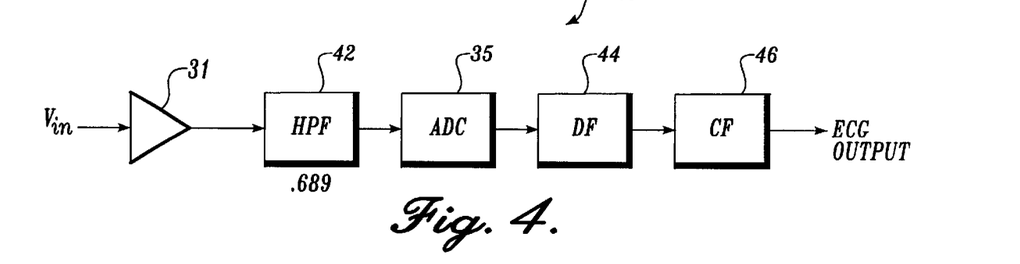
FIG. 4 is a block diagram illustrative of a digital ECG signal measuring system according to one embodiment of the present invention.

FIG. 4 is a block diagram illustrative of a digital ECG signal measuring system 40, according to one embodiment of the present invention. For clarity, the same reference numbers are used in the figures to indicate elements having the same or similar structure or function. In this embodiment, ECG signal measuring system 40 includes preamplifier 31, a HPF 42, an anti-aliasing filter (AAF) 48, ADC 35, a decimation filter (DF) 44, and a compensation filter (CF) 46.

Figure 5:
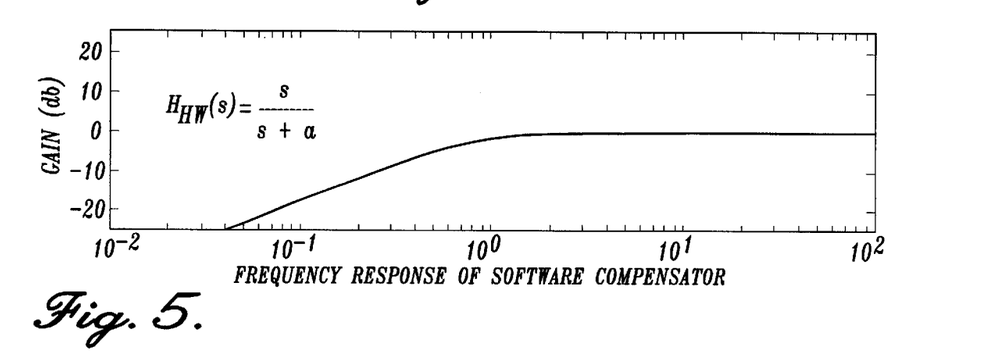
FIG. 5 is a graph illustrative of the frequency response of the high pass filter depicted in FIG. 4, according to one embodiment of the present invention.

ECG measuring system 40 is interconnected as follows. Preamplifier 31 is connected to receive the combined input signal via electrodes 15 and 16 (FIG. 1). Anti-aliasing filter (typically a LPF having a cutoff frequency less than one half of the sampling rate of the ADC) receives the output signal of preamplifier 31. Alternatively, anti-aliasing filter 48 can be placed anywhere in the signal processing flow before ADC 35. HPF 42 is connected to receive the output signal of anti-aliasing filter 48. In this embodiment, HPF 42 has a cutoff frequency of about 0.689 Hz, which is well into the AAMI specified ECG frequency bands (e.g., diagnostic and monitor). The frequency response of HPF 42 is illustrated in FIG. 5. In this embodiment, anti-aliasing filter 48 and HPF 42 are respectively implemented in hardware as a 3rd order Butterworth analog filter and a first order analog filter.

Referring back to FIG. 4, ADC 35 is connected to receive the output signal of HPF 42. In this embodiment, ADC 35 is implemented using a twelve-bit ADC, such as, for example, a model AD7892 available from Analog Devices, Norwood, MA, with a 5 ksps (kilo samples-per-second) sampling rate on each of a large number of sequentially selected channels. For an input signal with a 20 mV dynamic range, twelve-bit ADC 35 will output a digital output signal with 5 $\mu V$ resolution (i.e., a uniform 5 $\mu V$ step size). DF 44 is connected to receive the output samples from ADC 35. In this embodiment, DF 44 is a implemented as a 61-tap low-pass finite impulse response (FIR) filter implemented in software. In one embodiment, DF 44 computes a weighted running average of the ADC output samples, filters out the frequency components above 150 Hz, and outputs a 0.5 ksps data stream. In this embodiment, the decimation is performed by shifting the 5 ksps weighted running average samples into a shift register and selecting every tenth sample shifted out of the shift register to serve as the DF output data stream.

Figure 6:
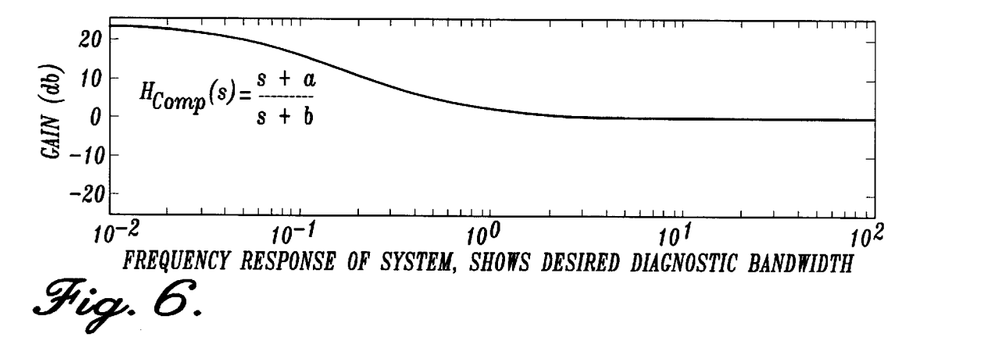
FIG. 6 is a graph illustrative of the frequency response of the compensation filter depicted in FIG. 4, according to one embodiment of the present invention.
Figure 7:
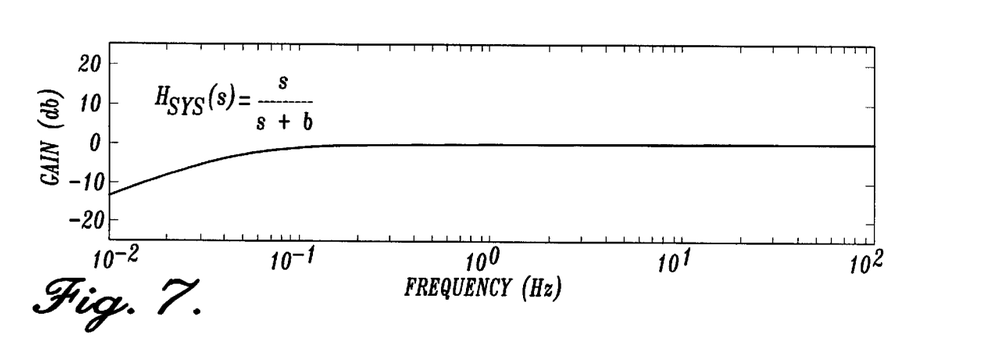
FIG. 7 is a graph illustrative of the frequency response of the system depicted in FIG. 4, according to one embodiment of the present invention.

CF 46 is connected to receive the output data stream from DF 44. CF 46 is implemented in software as a low pass digital filter with amplification or scaling of the output data stream. In this embodiment, the transfer function of CF 46 has a pole equal to the lower frequency boundary of the desired ECG output signal bandwidth (e.g., 0.05 Hz) and has a zero equal to the pole of HPF 42. The frequency response of CF 46 is illustrated in FIG. 6. Consequently, the frequency response of HPF 42 cascaded with CF 46 is equivalent to a LPF having a pole at the lower frequency boundary of the desired ECG output signal bandwidth as illustrated in FIG. 7.

Referring back to FIG. 4, ECG signal measuring system 40 operates as follows. Preamplifier 31 receives the combined input signal from electrodes 15 and 16 (FIG. 1). In this embodiment, the combined input signal has been filtered through AAF 48. HPF 42 then filters the amplified combined input signal outputted by preamplifier 31. In this embodiment, HPF 42 filters out frequency components of the amplified combined input signal below 0.689 Hz. A more specific statement of the operation of HPF 42 is:

$$H_{HPF}(\omega) = \frac{s}{(s+a)} \quad (1)$$

where $H_{HPF}(\omega)$ is the frequency response of HPF 42 and the variable "a" is the cutoff frequency of HPF 42 in radians. As will be appreciated by those skilled in the art, "a" is set to a frequency to attenuate the aforementioned baseline wander signal to prevent saturation of ADC 35. In the above embodiment, "a" is equal to about 2(0.689)π. In many ECG signal measuring systems that conform to current industry (AAMI) standards (e.g., the ECG signal measuring system of a LIFEPAK12 monitor/defibrillator available from Medtronic Physio-Control, Redmond, Wash.), "a" is greater than the required lower frequency boundary of the ECG output signal. Consequently, at this point of the signal processing, preventing saturation of ADC 35 comes at the cost of undesirably attenuating the lower frequency portion of the desired ECG output signal.

ADC 35 then samples the output signal from HPF 42. In this embodiment, ADC 35 samples at a rate of about 5 ksps, which is significantly greater than twice the maximum frequency boundary of the desired ECG signal band. Because HPF 42 attenuates the baseline wander signal, the signal received by ADC 35 has a dynamic range no greater than 20 mV, thereby preventing saturation of ADC 35. DF 44 then, as described above, low pass filters and reduces the sampling rate of the digital signal generated by ADC 35 to about 0.5 ksps.

CF 46 then, as described above, filters the output data stream from DF 44 to compensate for the attenuation of the ECG signal frequency components below the cutoff frequency of HPF 42 and above the minimum frequency boundary of the desired ECG signal band. This frequency band is referred to herein as the low-end band. In this embodiment, CF 46 provides a gain that is the inverse of the attenuation of the low-end band, which in this case is between 0.05 Hz and 0.689 Hz. A more specific statement of the operation of CF 46 is:

$$H_{CF}(\omega) = \frac{(s+a)}{(s+b)} \quad (2)$$

where $H_{CF}(\omega)$ is the frequency response of CF 46, the variable "b" is the desired low frequency boundary in radians of the ECG output signal, and variable "a" is as defined above in definition (1). In the above embodiment, "b" is equal to about $2(0.05)\pi$. Accordingly, the transfer function of HPF 42 cascaded with CF 46 is:

$$H_{SYS}(\omega) = \frac{s}{(s+b)} \quad (3)$$

where $H_{sys}(\omega)$ is the frequency response of HPF 42 cascaded with CF 46, and the variable "b" is as defined above in definition (2). It might appear that this compensation by CF 46 degrades the resolution of the system because the scaling of the low-end band also scales the step size. For example, if CF 46 amplifies a certain portion of the low-end band by ten, then the resolution of that portion would appear to be 25 $\mu$V. However, the inventors of the present invention have observed that the essentially random system or thermal noise injected into the combined input signal before ADC 35 has an average level greater than the step size or resolution of ADC 35. Thus, the system noise is, in effect, a dither signal that improves resolution by modulating some of the quantization error outside the frequency band of interest. In this way, dither techniques can be used to improve resolution below the least significant bit (e.g., see Vanderkooy and Lipshitz, "Resolution Below the Least Significant Bit it Digital Systems with Dither," J. Audio Eng. Soc., Vol. 32, No. 3, Mar., 1984, pp. 106–112). The output data stream of CF 48 is then displayed in analog form using conventional circuitry.

In light of this disclosure, those skilled in the art of sample data systems typified by ECG signal measuring systems will appreciate that dither techniques can improve the resolution beyond the improvement provided by oversampling alone. For example, oversampling provides about a half bit of increased resolution for each doubling of the sampling frequency. Thus, using oversampling alone would require an oversample ratio of about 256, resulting in a minimum sample rate of about 76.8 ksps to achieve four-bit resolution improvement. However, it can be shown that because the de-emphasis and enhancement is performed only on the low-end band, the oversampling ratio required to achieve the desired resolution is more strongly dependent on variable "b" rather than the upper frequency boundary of the desired ECG output signal. In particular, the desired resolution can be achieved by ensuring that the oversampling ratio is at least equal to:

$$1 + \frac{a^2}{b \cdot \omega_{upper}} \quad (4)$$

where $\omega_{upper}$ represents the upper frequency boundary in radians of the desired ECG output signal. This ensures that the quantization noise power is equivalent to that of a system which does not have the low-end frequency compensation. Thus, to achieve a resolution within 5 $\mu$V using the present invention, a minimum oversample ratio of about 1.06 is required, resulting in minimum sample rate of about 0.318 ksps. The 0.5 ksps data stream provided by DF 44 exceeds the required sample rate. There may be a system situation where a higher frequency "a" is required to maintain the desired dynamic range. In this case the oversampling rate is increased. For example with a HPF frequency of 5.0 Hz, the oversampling rate is calculated to be 4.33, resulting in a minimum sample rate of about 2.15 kHz.

Figure 8:
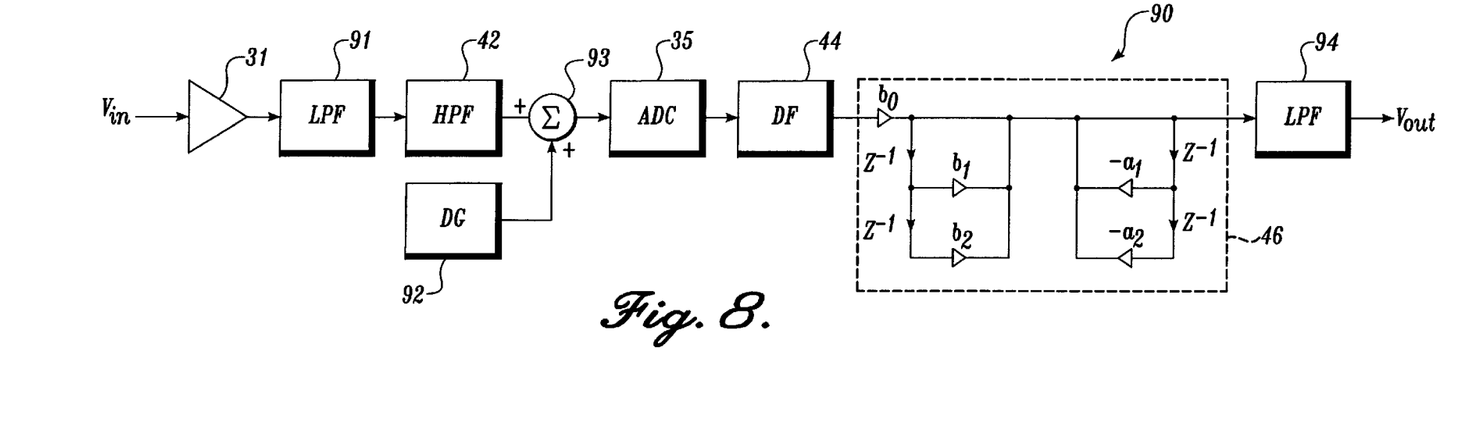
FIG. 8 is a block diagram illustrative of a digital ECG signal measuring system, according to another embodiment of the present invention.

FIG. 8 is a block diagram illustrative of a digital ECG signal measuring system 90, according to another embodiment of the present invention. ECG measuring system 90 is similar to ECG signal measuring system 40 (FIG. 4) except that ECG signal measuring system 90 shows the anti-aliasing filter as a LPF 91, and includes a dither generator (DG) 92, a hardware summer or combiner 93 and a LPF 94. DG 92 can be implemented with any suitable conventional signal generator. Further, in this embodiment, CF 46 is implemented in software with a standard biquad digital filter which utilizes summers, delays and multipliers.

ECG signal measuring system 90 is interconnected as follows. Preamplifier 31 is connected to receive the combined signal. LPF 91, functioning as an AAF, is connected to received the output signal from preamplifier 31 and provide its filtered output signal to HPF 42. Combiner 93 is connected to sum the output signal from HPF 42 and DG 92. ADC 35 is connected to receive the output signal from combiner 93 and provide its output samples to DF 44. CF 46 is connected to receive the data stream from DF 44. CF 46 then provides its output data stream to LPF 94. The output data stream of LPF 94 is then processed by conventional circuitry (not shown) to generate the ECG.

This embodiment of CF 46 is a standard two tap IIR filter with a Direct Form I structure, efficiently implemented in software. The transfer function of this filter is equivalent to that of definition (2). Another advantage of the embodiment of CF 46 is that the effective pole and zero of CF 46 can be easily changed "on-the-fly" by modifying calculation coefficients without inducing transients in the output of the filter. This allows operation of a fast restore function for baseline initialization after external transient events such as a defibrillation pulse.

ECG signal measuring system 90 operates essentially as described above for ECG signal measuring system 40 (FIG. 4) except that DG 92 adds a predetermined dither signal (e.g., a triangular wave with varying between lone half of the step size of ADC 35) instead of relying on system noise. This embodiment may be advantageously used in applications in which the system noise is small relative to the step size of the ADC. However, when DG 92 is configured to generate a known periodic dither signal, the dither signal can be used to shift the quantization noise out of the frequency range of interest.

LPF 94 is used to filter out the repeated or harmonic spectrums caused by the operation of the digitization process on the dithered signal. In addition, those skilled in the art will appreciate that interchanging the order of processing by DF 44 and CF 46 does not change the system response. Changing the order of processing in this manner would, however, increase the complexity and computing burden of the compensation filter by the ratio of the decimation.

Figure 9:
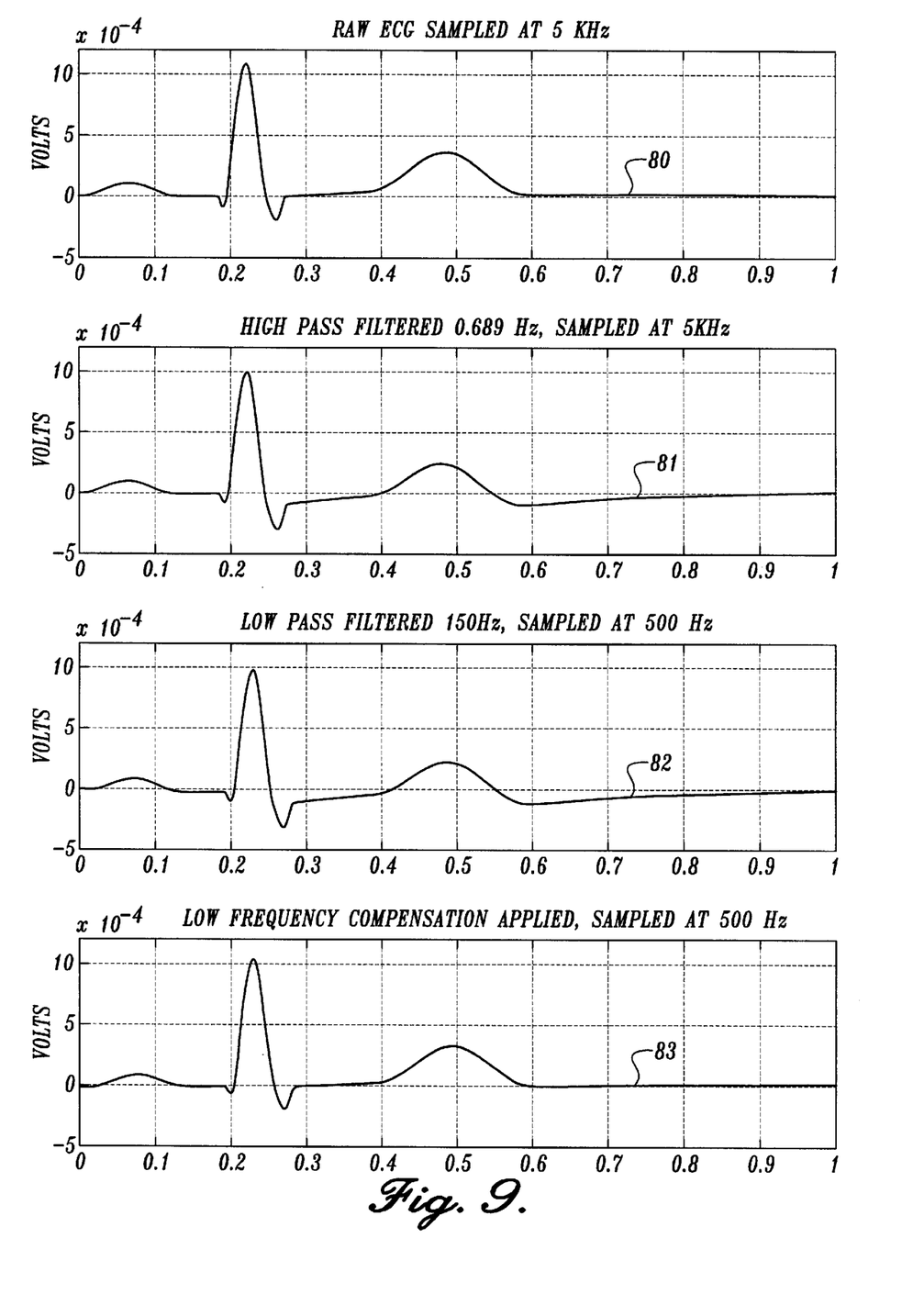
FIG. 9 is a graph illustrative of the ECG waveforms generated by the ECG signal measuring system of FIG. 9.

FIG. 9 shows the waveforms generated by a simulation of ECG signal measuring system 90. The input, or raw ECG, is shown as sampled at 5 ksps as a waveform 80. The output signal generated from HPF 42, set in this example at 0.689 Hz is shown as a waveform 81. Waveform 81 has a significant droop in slow moving parts of the waveform as is expected from a HPF with corner frequency in the band of interest. Decimation is accomplished in DF 44 which provides 150 Hz LPF at 500 sps shown as a waveform 82. The output signal generated from CF 46, shown as a waveform 83, is clearly nearly identical to the raw input waveform 80, maintaining the fidelity required for diagnostic interpretation of the ECG signals.

Figure 10:
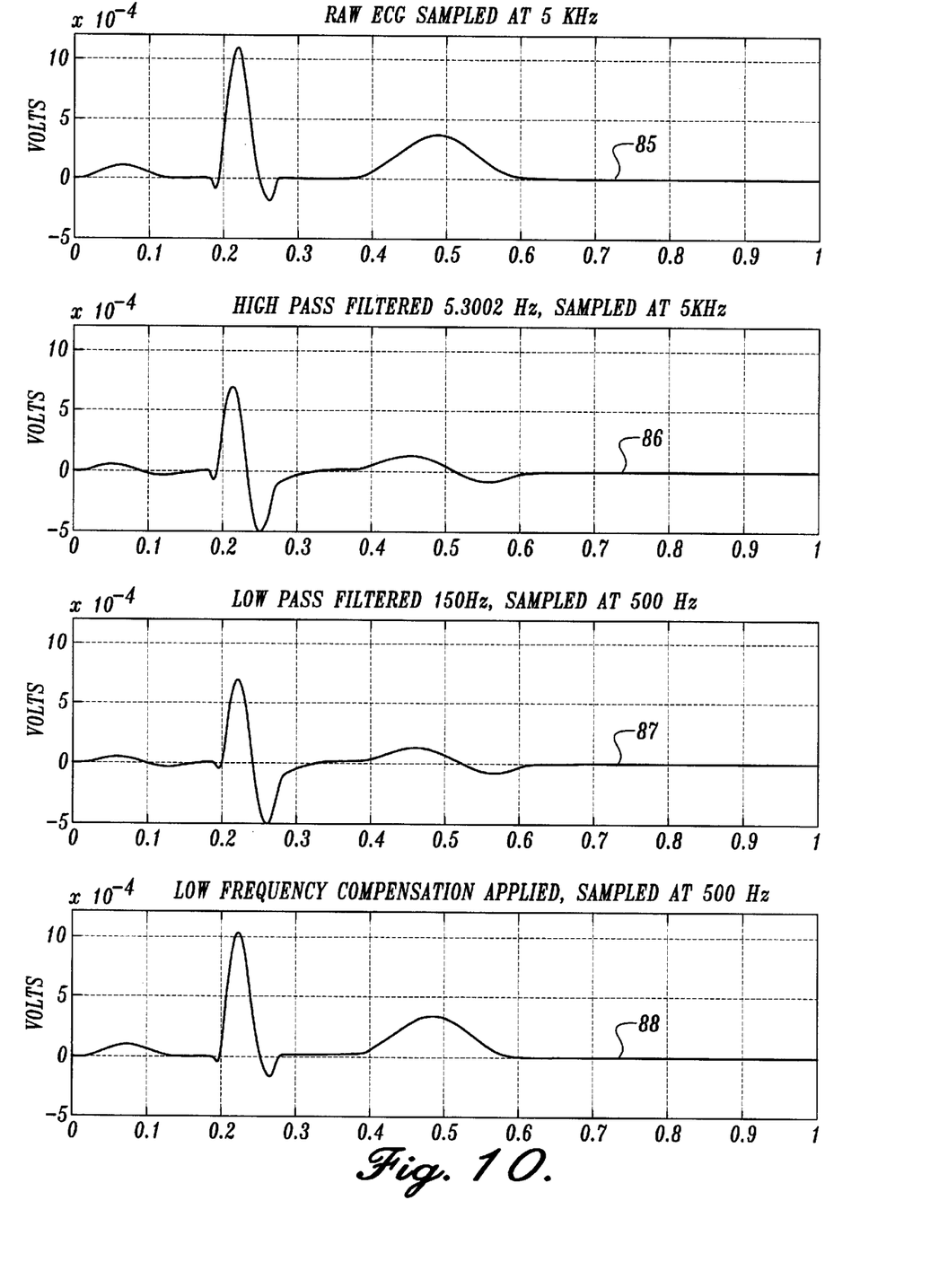
FIG. 10 a graph illustrative of the waveforms ECG generated by the ECG signal measuring system of FIG. 9 with a greater high pass filter corner frequency.

FIG. 10 shows the same waveforms as FIG. 9, but with HPF 42 and matching CF 44 corner frequencies set to 5.3 Hz. This results in even greater droop in intermediate waveforms 86 and 87, the output signals generated from HPF 42 and DF 44 respectively. The output signal generated from CF 46, shown as a waveform 88 has the same fidelity as the output waveform 83 of CF 46, also clearly nearly identical to the raw input waveform 80, maintaining the fidelity required for diagnostic interpretation of the ECG signals.

The embodiments of the ECG signal measuring system described above are illustrative of the principles of the present invention and are not intended to limit the invention to the particular embodiments described. For example, in light of the present disclosure, those skilled in the art can devise, without undue experimentation, embodiments using different implementations of the CF or different dither signals. In addition, those skilled in the art, in light of the present disclosure, can adjust the sampling rate and decimation ratio to accommodate different output ECG signal frequency bandwidths and low-end bands. Accordingly, while the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of filtering a sensed ECG signal from a patient in generating an output ECG signal having a predetermined frequency bandwidth, the method comprising:

filtering the input ECG signal with an anti-aliasing filter;

filtering an output signal from the anti-aliasing filter with a high pass filter (HPF), the cutoff frequency of the HPF being within the predetermined frequency bandwidth, wherein a low-band portion of the predetermined frequency bandwidth is attenuated;

sampling an output signal from the HPF to generate a stream of samples with a predetermined sample rate greater than twice the upper frequency of the predetermined frequency bandwidth;

decimating the stream of samples; and filtering the stream of samples with a compensation filter (CF), wherein the CF provides a gain for the low-band portion that is substantially equal to the inverse of the attenuation of the low-band portion.

2. The method of claim 1 wherein the CF is implemented in software.

3. The method of claim 1 further comprising combining a known dither signal with the output signal from the HPF.

4. The method of claim 3 wherein the dither signal has a dynamic range at least as great as the resolution of each sample of the stream of samples.

5. The method of claim 1 wherein the resolution of each sample of the stream of samples is within about 5 microvolts and the predetermined frequency bandwidth ranges from about 0.05 Hz to about 150 Hz.

6. The method of claim 5 wherein the sample rate is about 5000 samples per second.

7. The method of claim 5 wherein the HPF is implemented in hardware.

8. An ECG filter system for use in generating an output ECG signal having a predetermined frequency bandwidth in response to a sensed ECG signal from a patient, the system comprising:

an anti-aliasing filter coupled to receive the sensed ECG signal;

a high pass filter (HPF) coupled to the anti-aliasing filter, the HPF having a cutoff frequency within the predetermined frequency bandwidth, wherein the HPF is configured to attenuate a low-band portion of the predetermined frequency bandwidth;

an analog-to-digital converter (ADC) coupled to the HPF, the ADC being configured to generate a stream of samples with a predetermined sample rate greater than twice the upper frequency of the predetermined frequency bandwidth;

a compensation filter (CF) coupled to the ADC, wherein the CF is configured to provide a gain for the low-band portion that is substantially equal to the inverse of the attenuation of the low-band portion; and a decimator coupled to the CF.

9. The system of claim 8, wherein the CF comprises a digital filter implemented in software.

10. The system of claim 8, further comprising a dither generator circuit configured to combine a known dither signal with the output signal from the HPF.

11. The system of claim 10 wherein the dither signal has a dynamic range at least as great as the resolution of each sample of the stream of samples.

12. The system of claim 8 wherein the resolution of each sample of the stream of samples is within about 5 microvolts and the predetermined frequency bandwidth ranges from about 0.05 Hz to about 150 Hz.

13. The system of claim 12 wherein the sample rate is about 5000 samples per second.

14. The system of claim 12 wherein the HPF is implemented in hardware.

15. An ECG filter system for use in generating an output ECG signal having a predetermined frequency bandwidth in response to a sensed ECG signal from a patient, the system comprising:

an anti-aliasing filter coupled to receive the sensed ECG signal;

a high pass filter (HPF) coupled to the anti-aliasing filter, the HPF having a cutoff frequency within the predetermined frequency bandwidth, wherein the HPF is configured to attenuate a low-band portion of the predetermined frequency bandwidth;

an analog-to-digital converter (ADC) coupled to the HPF, the ADC being configured to generate a stream of samples with a predetermined sample rate greater than twice the upper frequency of the predetermined frequency bandwidth;

compensation means, coupled to the ADC, for digitally filtering the stream of samples, wherein the compensation means is configured to provide a gain for the low-band portion that is substantially equal to the inverse of the attenuation of the low-band portion; and decimation means, coupled to the compensation means.

16. The system of claim 15, wherein the CF is a digital filter implemented in software.

17. The system of claim 15 further comprising a dither generator circuit configured to combine a known dither signal with the output signal from the HPF.

18. The system of claim 17 wherein the dither signal has a dynamic range at least as great as the resolution of each sample of the stream of samples.

19. The system of claim 15 wherein the resolution of each sample of the stream of samples is within about 5 microvolts and the predetermined frequency bandwidth ranges from about 0.05 Hz to about 150 Hz.

20. The system of claim 19 wherein the HPF is implemented in hardware.

21. A defibrillator having an ECG filter system for use in generating an output ECG signal in response to an ECG signal from a patient, the output ECG signal having a predetermined frequency bandwidth, the defibrillator comprising:

a pair of electrodes, wherein the pair of electrodes is configured to provide a sensed ECG signal in response to signals generated by the patient's heart;

an anti-aliasing filter coupled to receive the sensed ECG signal;

a high pass filter (HPF) coupled to the anti-aliasing filter, the HPF having a cutoff frequency within the predetermined frequency bandwidth, wherein the HPF is configured to attenuate a low-band portion of the predetermined frequency bandwidth;

an analog-to-digital converter (ADC) coupled to the HPF, the ADC being configured to generate a stream of samples with a predetermined sample rate greater than twice the upper frequency of the predetermined frequency bandwidth;

a compensation filter (CF) coupled to the ADC, wherein the CF is configured to provide a gain for the low-band portion that is substantially equal to the inverse of the attenuation of the low-band portion;

a decimator coupled to the CF; and a display system coupled to the compensation filter, the display system being configured to display an ECG waveform in response to an output signal generated by the CF.

22. The defibrillator of claim 21, wherein the CF comprises a digital filter implemented in software.

23. The defibrillator of claim 21 further comprising a dither generator circuit configured to combine a known dither signal with the output signal from the HPF.

24. The defibrillator of claim 23 wherein the dither signal has a dynamic range at least as great as the resolution of each sample of the stream of samples.

25. The defibrillator of claim 21 wherein the HPF is implemented in hardware.

* * * * *

UNITED STATES PATENT AND TRADEMARK OFFICE
CERTIFICATE OF CORRECTION

PATENT NO. : 6,249,696 B1  
DATED : June 19, 2001  
INVENTOR(S) : D.J. Olson et al.

Page 1 of 1

It is certified that error appears in the above-identified patent and that said Letters Patent is hereby corrected as shown below:

Column 8,  
Line 45, "claim 8," should read -- claim 8 --

Signed and Sealed this

Fifth Day of March, 2002

Attest:

Attesting Officer

JAMES E. ROGAN  
Director of the United States Patent and Trademark Office